(12) United States Patent  
Araki et al.

(10) Patent No.: US 7,889,341 B2
(45) Date of Patent: Feb. 15, 2011

(54) MULTIPHOTON-EXCITATION LASER SCANNING MICROSCOPE

(75) Inventors: Makoto Araki, Tokyo (JP); Yasunari Matsukawa, Tokyo (JP); Hiroshi Sasaki, Tokyo (JP); Makio Ueno, Tokyo (JP)

(73) Assignee: Olympus Corporation, Tokyo (JP)

( * ) Notice: Subject to any disclaimer, the term of this patent is extended or adjusted under 35 U.S.C. 154(b) by 311 days.

(21) Appl. No.: 12/148,671

(22) Filed: Apr. 21, 2008

(65) Prior Publication Data

US 2008/0266551 A1    Oct. 30, 2008

(30) Foreign Application Priority Data

Apr. 26, 2007    (JP)    ............... 2007-117074

(51) Int. Cl.
*G01N 21/25*    (2006.01)

(52) U.S. Cl. .................. 356/417; 356/317; 356/73; 250/458.1; 250/234; 250/235

(58) Field of Classification Search ............ 250/458.1, 250/492.2, 234, 235, 459.1; 356/317–326, 356/73, 417

See application file for complete search history.

(56) References Cited

U.S. PATENT DOCUMENTS 6,555,781 B2 *    4/2003    Ngoi et al. ............... 359/285

7,372,985 B2 *    5/2008    So et al. ............... 382/133
2007/0109634 A1 *    5/2007    Araki et al. ............... 359/368

FOREIGN PATENT DOCUMENTS

JP    07-120680 A    5/1995
JP    2006-003521 A    1/2006

* cited by examiner

*Primary Examiner*—Gregory J Toatley
*Assistant Examiner*—Iyabo S Alli
(74) *Attorney, Agent, or Firm*—Holtz, Holtz, Goodman & Chick, PC (57) ABSTRACT

A multiphoton-excitation laser scanning microscope capable of efficiently collecting fluorescence emitted from a specimen to acquire a brighter multiphoton-excitation fluorescence image is provided. This multiphoton-excitation laser scanning microscope includes a multiphoton-excitation laser light source for emitting ultrashort pulsed laser light, a light-scanning unit configured to scan a specimen with the ultrashort pulsed laser light emitted from the multiphoton-excitation laser light source in two dimensions, an objective lens configured to focus the ultrashort pulsed laser light scanned by the light-scanning unit on the specimen, a collector lens disposed opposite the objective lens, with the light-scanning unit disposed therebetween, to collect fluorescence emitted from the specimen, and a light detector configured to detect the fluorescence collected by the collector lens. The collector lens has a higher numerical aperture and a larger field number than the objective lens.

14 Claims, 5 Drawing Sheets

MULTIPHOTON-EXCITATION LASER SCANNING MICROSCOPE

BACKGROUND OF THE INVENTION

1. Field of the Invention

The present invention relates to multiphoton-excitation laser scanning microscopes.

This application is based on Japanese Patent Application No. 2007-117074, the content of which is incorporated herein by reference.

2. Description of Related Art

Among known microscopes is a multiphoton-excitation microscope, which uses multiphoton excitation to acquire a bright fluorescence image of a specimen with high resolution in the depth direction (for example, see Japanese Unexamined Patent Application, Publication No. 2006-3521).

To avoid the problem of fluorescence emitted from a specimen as a result of multiphoton excitation being attenuated before being detected by a light detector because of loss caused when it passes through a plurality of optical elements such as mirrors and lenses, the multiphoton-excitation microscope according to Japanese Unexamined Patent Application, Publication No. 2006-3521 includes a light detector disposed at a position reached by the fluorescence after it passes through only an objective lens and a dichroic mirror, thus acquiring a bright multiphoton-excitation fluorescence image with reduced fluorescence loss.

Of the fluorescence emitted from the specimen in all directions, however, the fluorescence collected by the objective lens is limited by the numerical aperture of the objective lens. This poses a problem in that the emitted fluorescence cannot be efficiently detected unless the numerical aperture of the objective lens can be increased. For electrophysiological experiments, for example, in which a needle, as used in a patch clamp, is often inserted near the examination site on a specimen, the tip angle of the objective lens cannot be increased because it would otherwise interfere with the needle. Hence, an objective lens with high numerical aperture cannot be used.

BRIEF SUMMARY OF THE INVENTION

The present invention provides a multiphoton-excitation laser scanning microscope capable of efficiently collecting fluorescence emitted from a specimen as a result of multiphoton excitation to acquire a brighter multiphoton-excitation fluorescence image.

The present invention provides a multiphoton-excitation laser scanning microscope including a multiphoton-excitation laser light source configured to emit ultrashort pulsed laser light, a light-scanning unit configured to scan a specimen with the ultrashort pulsed laser light emitted from the multiphoton-excitation laser light source in two dimensions, an objective lens configured to focus the ultrashort pulsed laser light scanned by the light-scanning unit on the specimen, a collector lens disposed opposite the objective lens, with the specimen disposed therebetween, to collect fluorescence emitted from the specimen as a result of multiphoton excitation, and a light detector configured to detect the fluorescence collected by the collector lens. The collector lens has a higher numerical aperture and a larger field number than the objective lens.

According to the present invention, the light-scanning unit scans the specimen with the ultrashort pulsed laser light emitted from the multiphoton-excitation laser light source in two dimensions. The laser light is focused on the specimen through the objective lens. This induces multiphoton excitation at the focus position of the ultrashort pulsed laser light, thus causing fluorescence to be emitted. Of the fluorescence emitted, fluorescence passing through the specimen is collected by the collector lens and is detected by the light detector. Thus, a multiphoton-excitation fluorescence image can be created based on the intensity of the fluorescence detected by the light detector and the scanning position of the ultrashort pulsed laser light with the light-scanning unit.

In this case, the collector lens, having a higher numerical aperture and a larger field number than the objective lens, can more efficiently collect the fluorescence than the objective lens. In particular, its large field number enables efficient collection of fluorescence scattered in a thick specimen, which readily scatters light, thus acquiring a bright multiphoton-excitation fluorescence image.

In the above invention, the light detector may be a side-on photomultiplier tube.

This allows sensitive detection of weak fluorescence without leakage.

In the above invention, additionally, the multiphoton-excitation laser scanning microscope may further include an optical-path splitter configured to split the fluorescence collected by the collector lens based on wavelength, and fluorescence having different wavelengths may be split by the optical-path splitter and may be detected by a plurality of respective light detectors.

Detection of the fluorescence having different wavelengths emitted from the specimen allows simultaneous examination by, for example, multiple staining using a plurality of fluorescent dyes.

In the above invention, additionally, the multiphoton-excitation laser scanning microscope may further include two or more excitation-light cutting filters disposed between the collector lens and the light detector at a certain distance from each other in an optical-axis direction.

The excitation-light cutting filters can block the ultrashort pulsed laser light passing through the specimen to prevent its entry into the light detector. Any ultrashort pulsed laser light leaking without being blocked by one excitation-light cutting filter can be blocked by the other excitation-light cutting filter disposed at a certain distance therefrom.

In the above invention, additionally, the multiphoton-excitation laser scanning microscope may further include an absorbing filter between the excitation-light cutting filters.

With this configuration, the absorbing filter disposed between the two excitation-light cutting filters can absorb repeated reflections between the two excitation-light cutting filters, thus more effectively preventing leakage of the ultrashort pulsed laser light to the light detector side.

In the above invention, additionally, the multiphoton-excitation laser scanning microscope may further include a transmitted-illumination light source configured to emit transmitted-illumination light with which the specimen is irradiated through the collector lens and a mirror insertable into and removable from an optical path between the collector lens and the light detector. The mirror may be configured to switch between an optical path from the collector lens to the light detector and an optical path from the transmitted-illumination light source to the collector lens.

With this configuration, inserting and removing the mirror into and from the optical path between the collector lens and the light detector allows easy switching between the two optical paths to carry out multiphoton-excitation fluoroscopy and transmission observation. If the transmission observation is selected, the specimen can be examined by irradiating the specimen with the transmitted-illumination light emitted from the transmitted-illumination light source through the collector lens and collecting light passing through the specimen with the objective lens. In addition, the optical path can be deflected at an angle of 90° by inserting the mirror at a tilt angle of 45° with respect to the optical path. Deflecting the optical path ensures sufficient installation space for the optical system, including the light detector, if only a small space is left in a direction along the optical axis of the collector lens.

In the above invention, additionally, the multiphoton-excitation laser scanning microscope may further include a pupil-relay optical system disposed between the collector lens and the light detector so that the position of the light detector is conjugate with respect to a pupil position of the collector lens.

With this configuration, the pupil-relay optical system allows the pupil plane of the collector lens to be projected onto the light detector. As a result, the light detector can always receive the fluorescence at the same position as the ultrashort pulsed laser light is shifted across the specimen. This prevents fluctuations in the intensity of light detected on a light-receiving surface of the light detector due to variations in sensitivity, so that a uniform-brightness multiphoton-excitation fluorescence image can be acquired.

In the above invention, additionally, the collector lens and the light detector may be movable together as a single unit.

This allows the collector lens to be maintained at the optimum position with respect to the light detector for multiphoton-excitation observation.

In the above invention, additionally, the collector lens and the light detector may be movable in an optical-axis direction of the objective lens.

This eliminates the need to adjust the positions of the collector lens and the light detector after each focus adjustment of the collector lens, thus saving trouble in examination.

In the above invention, additionally, the collector lens and the light detector may be movable in a direction perpendicular to the optical axis of the objective lens.

This eliminates the need to adjust the positions of the collector lens and the light detector after each optical-axis adjustment of the collector lens, thus saving trouble in examination.

In the above invention, additionally, the multiphoton-excitation laser scanning microscope may further include an epi-illumination light source configured to emit epi-illumination light with which the specimen is irradiated through the objective lens and a detected-light attenuating unit configured to reduce the intensity of light detected by the light detector upon irradiation of the specimen with the epi-illumination light from the epi-illumination light source.

With this configuration, the detected-light attenuating unit can operate to prevent damage to the light detector due to the epi-illumination light, which is intense, by reducing the intensity of light detected by the light detector upon irradiation of the specimen with the epi-illumination light from the epi-illumination light source. The detected-light attenuating unit used may be a shutter configured to open and close the optical path between the collector lens and the light detector, a voltage-adjusting unit configured to reduce the voltage applied to the light detector, or a switching mirror configured to switch between the optical path toward the light detector and another optical path.

In the above invention, additionally, the collector lens may be a liquid-immersion lens with oil filling a gap between the specimen and the collector lens.

With the oil filling the gap between the specimen and the collector lens in this way, the collector lens can achieve a higher numerical aperture.

In the above invention, additionally, the light detector may be disposed on an extension of the optical axis of the collector lens.

This eliminates the need to use optical elements that cause loss, such as a deflecting mirror, thus allowing efficient collection of fluorescence with a simplified structure.

In the above invention, additionally, the light detector may include a plurality of light detector elements arranged in a two-dimensional array.

With this configuration, the light detector elements, arranged over a wide area, can detect the fluorescence collected by the collector lens, which has a high numerical aperture and large field number, with a large beam diameter, so that they can be disposed near the collector lens to achieve size reduction on the collector lens side. In addition, it is possible to eliminate the need to use a lens such as a pupil-relay lens, thus reducing losses, so that a brighter multiphoton-excitation fluorescence image can be acquired.

The present invention thus has the advantage of efficiently collecting the fluorescence emitted from the specimen to acquire a brighter multiphoton-excitation fluorescence image.

DETAILED DESCRIPTION OF THE INVENTION

A multiphoton-excitation laser scanning microscope 1 according to an embodiment of the present invention will now be described with reference to FIGS. 1 and 2.

Figure 1:
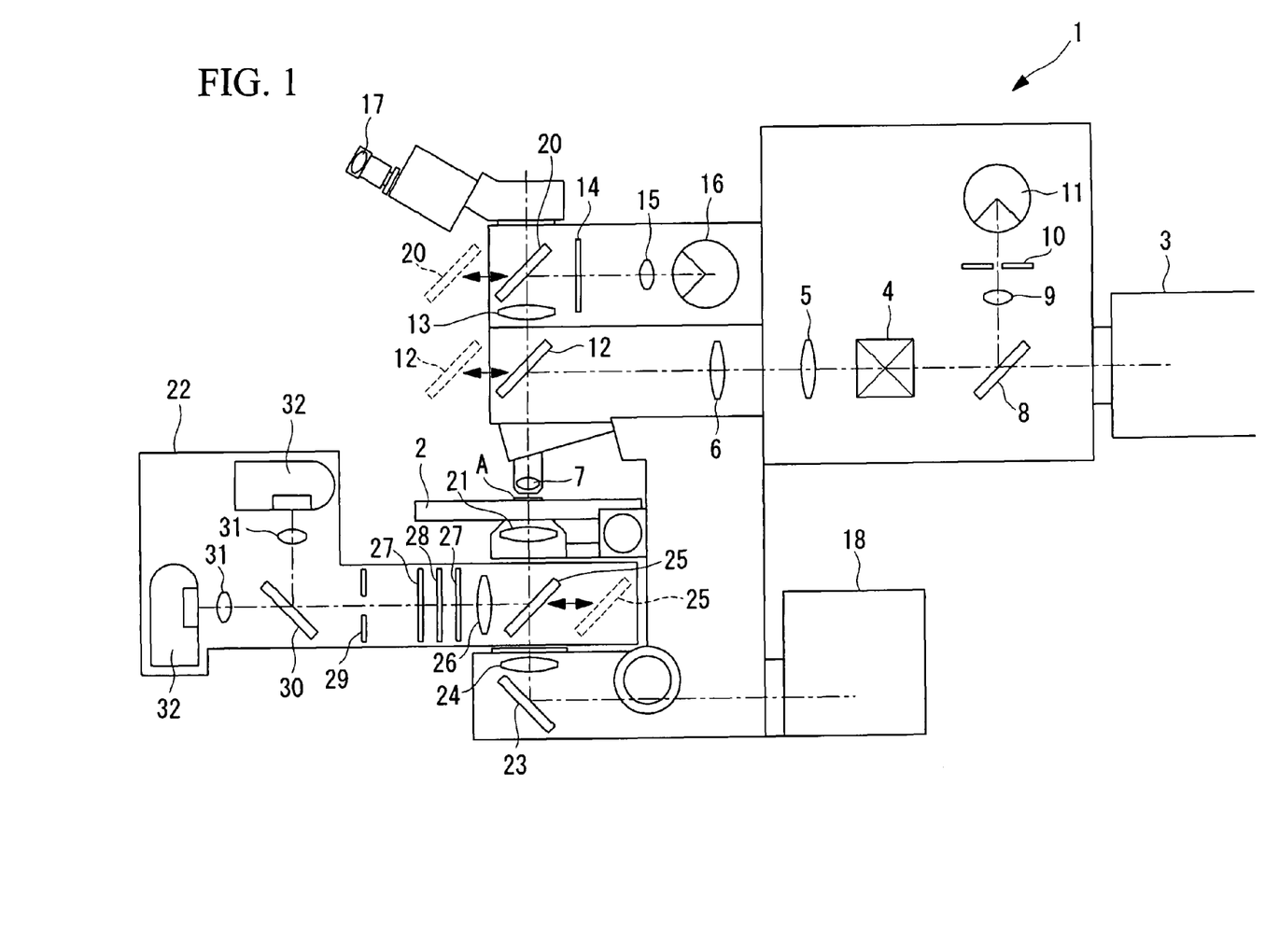
FIG. 1 is a diagram showing the overall configuration of a multiphoton-excitation laser scanning microscope according to an embodiment of the present invention.

Referring to FIG. 1, the multiphoton-excitation laser scanning microscope 1 according to this embodiment is a microscope capable of two types of multiphoton-excitation fluoroscopy as well as confocal fluoroscopy and transmitted illumination observation. This multiphoton-excitation laser scanning microscope 1 includes a stage 2 on which a specimen A is placed; a laser light source 3 configured to emit ultrashort pulsed laser light and continuous laser light to a space above the stage 2; a scanner (light-scanning unit) 4 configured to scan the specimen A with the laser light emitted from the laser light source 3 in two dimensions; a pupil projection lens 5 and an image-forming lens 6 configured to converge the scanned laser light; and an objective lens 7 configured to focus the laser light converged by the image-forming lens 6 so that it irradiates the specimen A.

In addition, the multiphoton-excitation laser scanning microscope 1 includes, above the stage 2, a dichroic mirror 8 configured to split off fluorescence emitted from the specimen A from the laser light after the fluorescence passes through the objective lens 7, the image-forming lens 6, the pupil projection lens 5, and the scanner 4; a confocal lens 9 configured to focus the fluorescence split off by the dichroic mirror 8; a confocal pinhole 10 disposed near the focus position of the confocal lens 9; and a light detector 11 configured to detect the fluorescence passing through the confocal pinhole 10.

The multiphoton-excitation laser scanning microscope 1 further includes, above the stage 2, a dichroic mirror 12 configured to split off fluorescence that is emitted from a position where the ultrashort pulsed laser light is focused on the specimen A and that is collected by the objective lens 7 from the optical path of the ultrashort pulsed laser light; an image-forming lens 13 configured to focus the split fluorescence; an excitation-light cutting filter 14 configured to block ultrashort pulsed laser light contained in the fluorescence focused by the image-forming lens 13; a collector lens 15 configured to collect the fluorescence; and a light detector 16 configured to detect the collected fluorescence.

In FIG. 1, reference numeral 17 denotes an eyepiece lens for use in transmission observation with illumination light from a transmitted-illumination light source 18 to be described later, and reference numeral 20 denotes a mirror that is removed from the optical path when performing transmission observation through the eyepiece lens 17. The dichroic mirror 12 is also removed from the optical path when performing transmission observation.

In addition, the multiphoton-excitation laser scanning microscope 1 according to this embodiment includes, below the stage 2, a collector lens 21 disposed opposite the objective lens 7 with the specimen A therebetween; a multiphoton-transmission detector unit 22 configured to detect the fluorescence collected by the collector lens 21; and the transmitted-illumination light source 18, a mirror 23, and a window lens 24, which are configured to irradiate the bottom of the specimen A with transmitted-illumination light through the collector lens 21.

Figure 2:
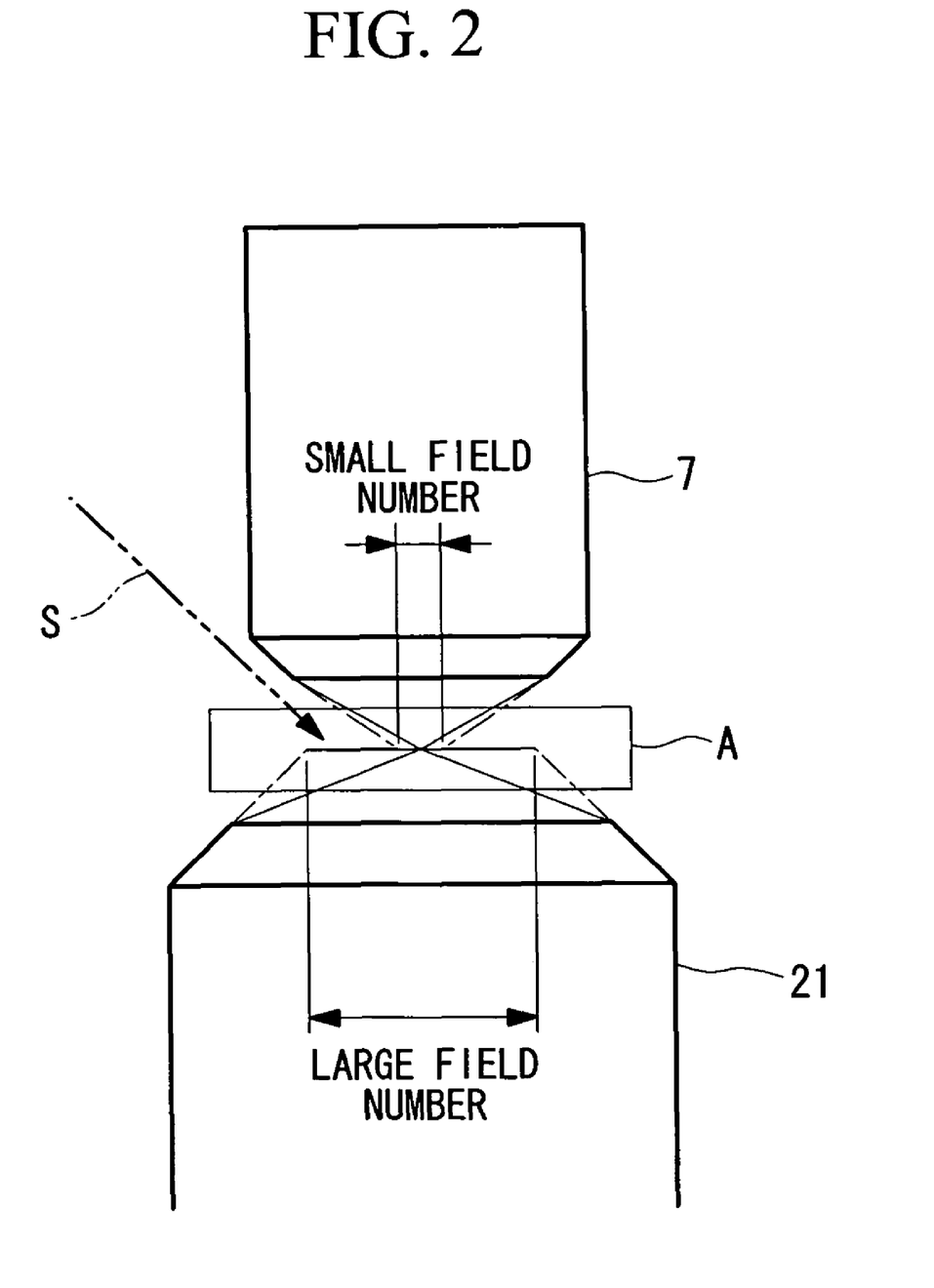
FIG. 2 is a diagram illustrating the relationship between an objective lens and a collector lens of the multiphoton-excitation laser scanning microscope of FIG. 1.

Referring to FIG. 2, the collector lens 21 has a higher numerical aperture and a larger field number than the objective lens 7.

Referring back to FIG. 1, the multiphoton-transmission detector unit 22 includes a mirror 25 configured to reflect the fluorescence collected by the collector lens 21 at an angle of 90°, an image-forming lens 26, two excitation-light cutting filters 27, an absorbing filter 28, a shutter 29, a dichroic mirror 30 configured to split the fluorescence based on wavelength, two collector lenses 31, and two light detectors 32.

The mirror 25 can be inserted into and removed from the optical path. If the mirror 25 is inserted into the optical path, the mirror 25 reflects the fluorescence collected by the collector lens 21 and directs it into an optical path toward the light detectors 32. If the mirror 25 is removed from the optical path, the optical path is switched such that transmitted-illumination light emitted from the transmitted-illumination light source 18 is guided into the collector lens 21 by the mirror 23 and the window lens 24.

The two excitation-light cutting filters 27 are disposed at a certain distance from each other in the optical-axis direction with the absorbing filter 28 disposed therebetween. This arrangement allows the two excitation-light cutting filters 27 to effectively block the ultrashort pulsed laser light and the absorbing filter 28 disposed therebetween to absorb repeated reflections between the two excitation-light cutting filters 27, thus more effectively preventing leakage of the ultrashort pulsed laser light to the light detector 32 side.

The shutter 29 is opened only when the collector lens 21 collects the fluorescence emitted from the bottom of the specimen A upon irradiation of the specimen A with the ultrashort pulsed laser light and is closed in other situations.

All the light detectors 32 used are side-on photomultiplier tubes, which can detect fluorescence with high sensitivity.

The operation of the multiphoton-excitation laser scanning microscope 1 according to this embodiment, thus configured, will now be described.

In multiphoton-excitation fluoroscopy using the multiphoton-excitation laser scanning microscope 1 according to this embodiment, the scanner 4 scans the specimen A with the ultrashort pulsed laser light emitted from the laser light source 3 in two dimensions. The laser light is focused on the specimen A through the pupil projection lens 5, the image-forming lens 6, and the objective lens 7. Fluorescence is then emitted from a position where the ultrashort pulsed laser light is focused on the specimen A.

The fluorescence emitted downward from the specimen A is collected by the collector lens 21, is deflected at an angle of 90° by the mirror 25, is focused by the image-forming lens 26, and is extracted from the ultrashort pulsed laser light by the excitation-light cutting filters 27 and the absorbing filter 28. The fluorescence is then split by the dichroic mirror 30 based on wavelength before being detected by the respective light detectors 32. Thus, a two-dimensional multiphoton-excitation fluorescence image can be created for each wavelength based on the intensity of the fluorescence detected by the light detectors 32 and the scanning position of the scanner 4 upon emission of the fluorescence.

For the multiphoton-excitation laser scanning microscope 1 according to this embodiment, as shown in FIG. 2, the collector lens 21 has a higher numerical aperture and a larger field number than the objective lens 7. The microscope 1 can therefore collect more fluorescence to acquire a brighter multiphoton-excitation fluorescence image.

In the multiphoton-excitation fluoroscopy, the objective lens 7 requires optical performance with high precision in order to precisely set the scanning position and depth where the ultrashort pulsed laser light is focused. Such high precision, however, is not necessarily required for detection of the fluorescence emitted; rather, maximizing the intensity of light detected is required.

Hence, for the collector lens 21 on the detection side, the use of a lens with a higher numerical aperture and a larger field number than the objective lens 7 allows collection of more of the fluorescence emitted in all directions from the focus position of the ultrashort pulsed laser light. In particular, increasing the field number is advantageous for examination of a specimen A such as a sliced brain specimen, which is relatively thick and strongly scatters light, because the collector lens 21 can also efficiently collect fluorescence returning to its field of view after being scattered.

In addition, a sharp multiphoton-excitation fluorescence image can be acquired even if a lens with a reduced diameter is used as the objective lens 7 so that it does not interfere with a needle S, as used in a patch clamp, to be inserted near the examination site on the specimen A.

In the multiphoton-excitation laser scanning microscope 1 according to this embodiment, additionally, the pupil position of the collector lens 21 is coincident with light-receiving surfaces of the light detectors 32 when the fluorescence collected by the collector lens 21 is guided into the light detectors 32 through the image-forming lens 26 and the collector lenses 31. As a result, the light detectors 32 can always receive the fluorescence at the same positions as the scanner 4 scans the focus position of the ultrashort pulsed laser light. Thus, even if the light-receiving surfaces of the light detectors 32 have variations in sensitivity, a uniform-brightness multiphoton-excitation fluorescence image which is not affected by the variations can be acquired.

In addition, the use of side-on photomultiplier tubes, which have high sensitivity, as the light detectors 32 allows acquisition of a bright multiphoton-excitation fluorescence image.

In addition, the two excitation-light cutting filters 27 are disposed at a certain distance from each other, with the absorbing filter 28 disposed therebetween. This arrangement can effectively block even the ultrashort pulsed laser light, which has relatively high intensity, entering the optical path on the detection side, thus preventing it from entering the light detectors 32.

In addition, the shutter 29 is opened only when the collector lens 21 collects the fluorescence emitted from the bottom of the specimen A upon irradiation of the specimen A with the ultrashort pulsed laser light and is closed in other situations. The shutter 29 can therefore prevent entry of intense light whose intensity exceeds a detection range with the light detectors 32 activated, thus preventing damage to the light detectors 32.

In addition, fluorescence generated in the specimen A and emitted upward above the stage 2 is collected by the objective lens 7. The fluorescence collected by the objective lens 7 is split off from the ultrashort pulsed laser light by the dichroic mirror 12 and is detected by the light detector 16 after passing through the image-forming lens 13, the mirror 20, the excitation-light cutting filter 14, and the collector lens 15. When the fluorescence is collected by the objective lens 7, it cannot be efficiently collected as compared to the multiphoton-transmission detector unit 22. However, a relatively bright multiphoton-excitation fluorescence image can be acquired if the focus position of the ultrashort pulsed laser light lies near the top surface of the specimen A. In this case, the shutter 29 is closed, thus preventing the fluorescence from entering the light detectors 32.

In confocal observation of the specimen A, continuous laser light is emitted from the laser light source 3, and the continuous laser light scanned at the scanner 4 is focused on the specimen A through the pupil projection lens 5, the image-forming lens 6, and the objective lens 7. Focusing the continuous laser light causes fluorescence to be emitted from the specimen A. The fluorescence, passing through the objective lens 7, the image-forming lens 6, the pupil projection lens 5, and the scanner 4, is split off from the optical path of the continuous laser light by the dichroic mirror 8 and is focused by the confocal lens 9. The light detector 11 detects only fluorescence passing through the confocal pinhole 10. Thus, a sectional fluorescence image of the specimen A extending over the focal plane of the objective lens 7 can be acquired. In this case, the shutter 29 is closed, thus preventing the fluorescence from entering the light detectors 32.

In transmission observation of the specimen A, the transmitted-illumination light source 18 operates with the mirror 25 of the multiphoton-transmission detector unit 22, the dichroic mirror 12, and the mirror 20 removed from the optical path and the shutter 29 closed. The transmitted-illumination light source 18 emits transmitted-illumination light which is deflected vertically upward by the mirror 23 and is focused on the specimen A through the window lens 24 and the collector lens 21. Transmitted-illumination light passing through the specimen A is collected by the objective lens 7 and the image-forming lens 13 and is guided to the eyepiece lens 17, thus allowing visual observation of the specimen A.

For the multiphoton-excitation laser scanning microscope 1 according to this embodiment, the shutter 29 is used to prevent entry of intense light into the light detectors 32, although the present invention is not limited thereto, and detection sensitivity may instead be decreased by reducing the voltage applied to the light detectors 32.

In addition, the use of a liquid-immersion lens as the collector lens 21 is effective because a higher numerical aperture can be achieved by filling the gap between the collector lens 21 and the specimen A with oil.

Figure 3:
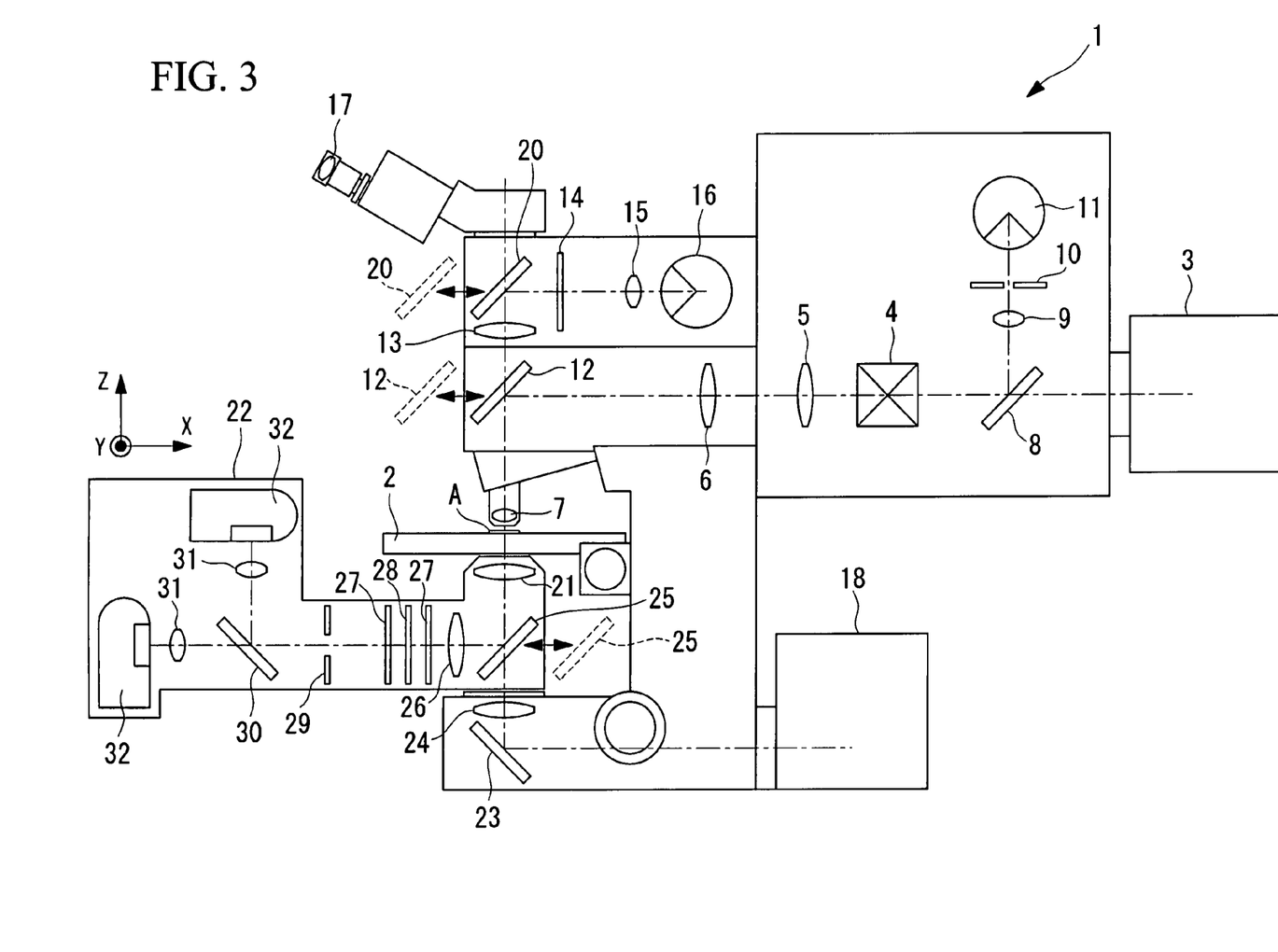
FIG. 3 is a diagram showing the overall configuration of a first modification of the multiphoton-excitation laser scanning microscope of FIG. 1.

Referring to FIG. 3, additionally, the multiphoton-transmission detector unit 22 and the collector lens 21 may be integrated such that they are movable in the optical-axis direction (Z direction) of the collector lens 21 and two directions (X and Y directions) perpendicular to the optical-axis direction. This allows focus adjustment and optical-axis adjustment of the collector lens 21 while maintaining the optimum positional relationship between the collector lens 21 and the light detectors 32.

Figure 4:
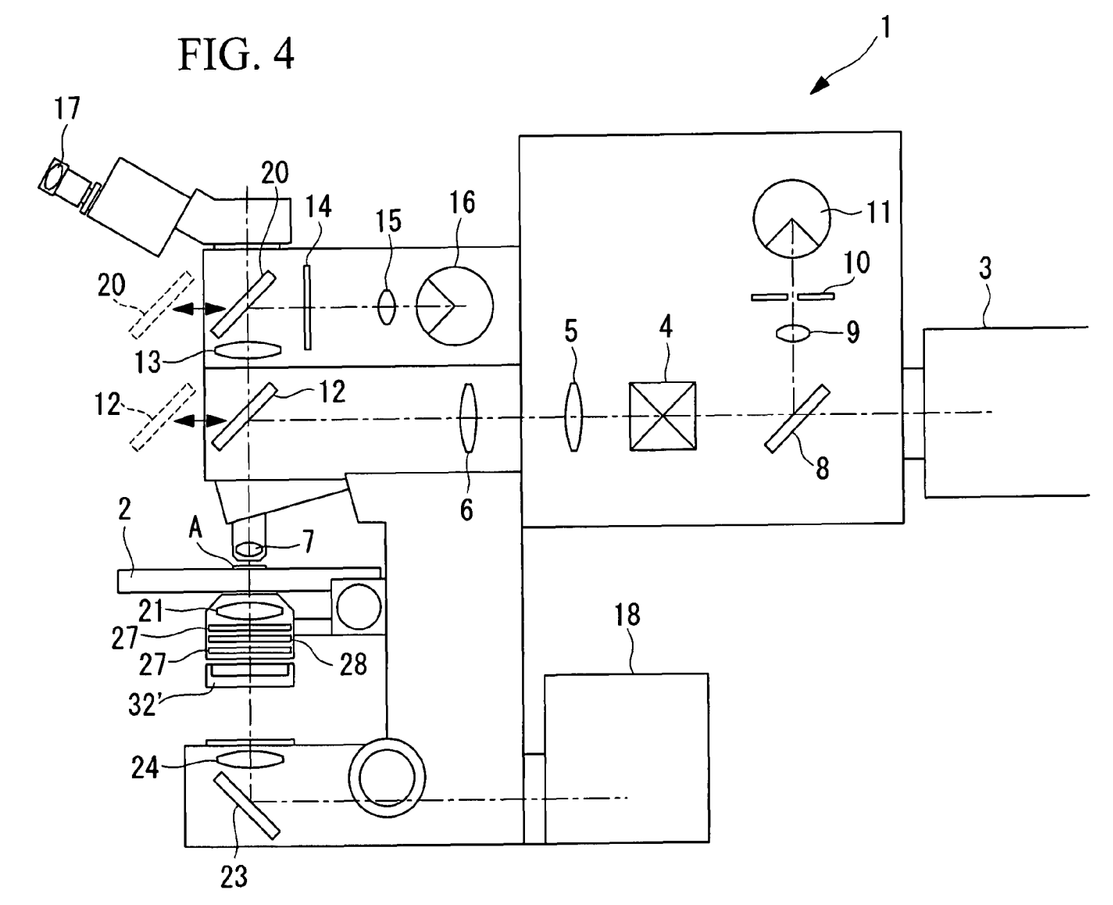
FIG. 4 is a diagram showing the overall configuration of a second modification of the multiphoton-excitation laser scanning microscope of FIG. 1.
Figure 5:
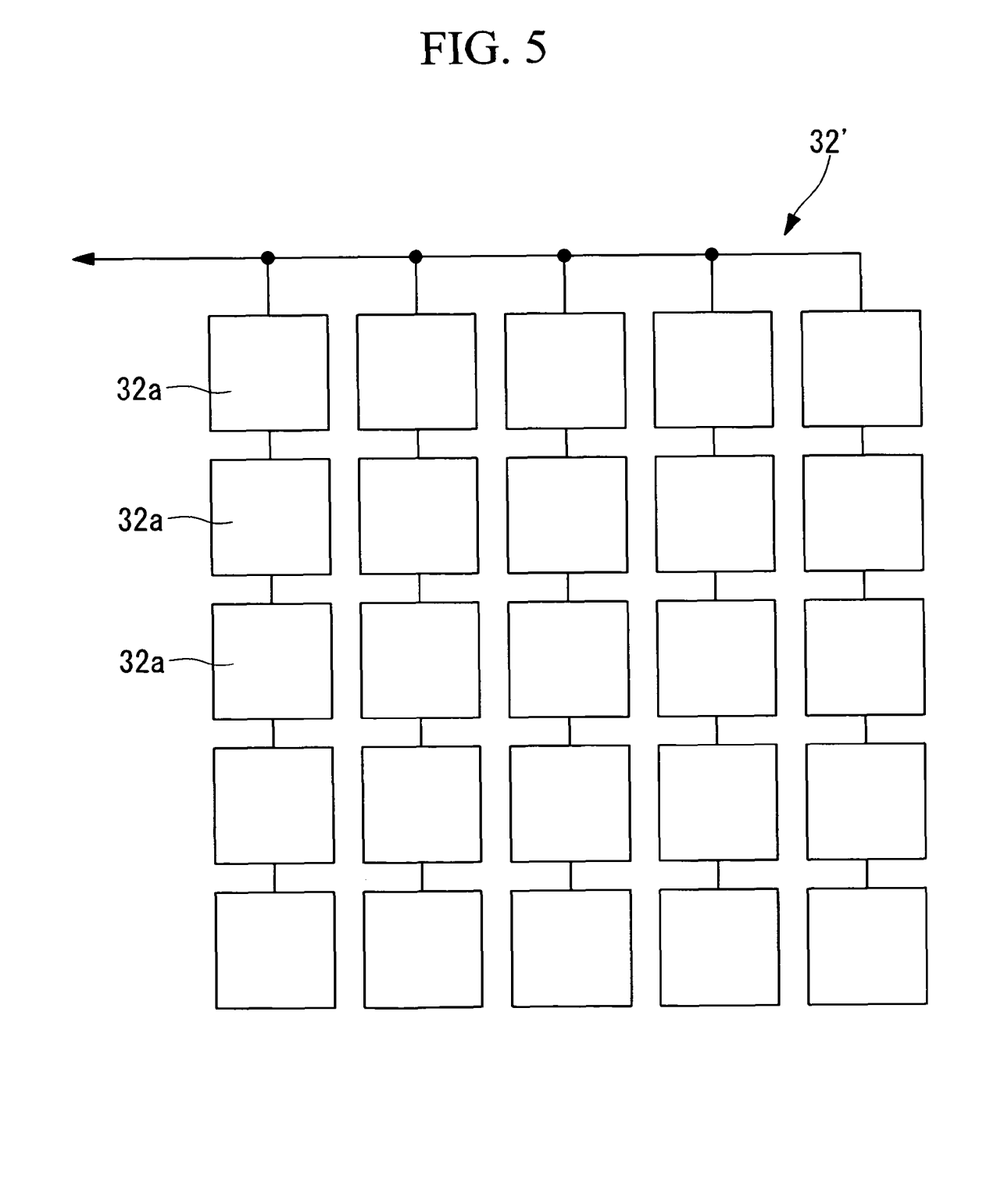
FIG. 5 is a diagram showing an example of a light detector used in the multiphoton-excitation laser scanning microscope of FIG. 4.

Referring to FIG. 4, additionally, a light detector 32' may instead be disposed on an extension of the optical axis of the collector lens 21. In this case, the light detector 32' detects the fluorescence collected by the collector lens 21, which has a high numerical aperture and large field number, at a position where the fluorescence has a large beam diameter. As shown in FIG. 5, the light detector 32' used may include a two-dimensional array of light detector elements 32a, and detection signals generated by the light detector elements 32a may be combined.

What is claimed is:

1. A multiphoton-excitation laser scanning microscope comprising:
   a multiphoton-excitation laser light source configured to emit ultrashort pulsed laser light;
   a light-scanning unit configured to scan the ultrashort pulsed laser light emitted from the multiphoton-excitation laser light source in two dimensions;
   an objective lens configured to focus the ultrashort pulsed laser light scanned by the light-scanning unit on the specimen;
   a collector lens disposed opposite the objective lens, with the specimen disposed therebetween, to collect fluorescence emitted from the specimen as a result of multiphoton excitation; and
   a light detector configured to detect the fluorescence collected by the collector lens;
   wherein the collector lens has a higher numerical aperture and a larger field number than the objective lens.

2. The multiphoton-excitation laser scanning microscope according to claim 1, wherein the light detector is a side-on photomultiplier tube.

3. The multiphoton-excitation laser scanning microscope according to claim 1, further comprising an optical-path splitter configured to split the fluorescence collected by the collector lens based on wavelength;
   wherein fluorescence having different wavelengths is split by the optical-path splitter and is detected by a plurality of respective light detectors.

4. The multiphoton-excitation laser scanning microscope according to claim 1, further comprising two or more excitation-light cutting filters disposed between the collector lens and the light detector at a certain distance from each other in an optical-axis direction.

5. The multiphoton-excitation laser scanning microscope according to claim 4, further comprising an absorbing filter between the excitation-light cutting filters.

6. The multiphoton-excitation laser scanning microscope according to claim 1, further comprising:

a transmitted-illumination light source configured to emit transmitted-illumination light with which the specimen is irradiated through the collector lens; and a mirror insertable into and removable from an optical path between the collector lens and the light detector, the mirror being configured to switch between an optical path from the collector lens to the light detector and an optical path from the transmitted-illumination light source to the collector lens.

7. The multiphoton-excitation laser scanning microscope according to claim 1, further comprising a pupil-relay optical system disposed between the collector lens and the light detector so that the position of the light detector is conjugate with respect to a pupil position of the collector lens.

8. The multiphoton-excitation laser scanning microscope according to claim 1, wherein the collector lens and the light detector are movable together as a single unit.

9. The multiphoton-excitation laser scanning microscope according to claim 8, wherein the collector lens and the light detector are movable in an optical-axis direction of the objective lens.

10. The multiphoton-excitation laser scanning microscope according to claim 8, wherein the collector lens and the light detector are movable in a direction perpendicular to the optical axis of the objective lens.

11. The multiphoton-excitation laser scanning microscope according to claim 1, further comprising:

an epi-illumination light source configured to emit epi-illumination light with which the specimen is irradiated through the objective lens; and a detected-light attenuating unit configured to reduce the intensity of light detected by the light detector upon irradiation of the specimen with the epi-illumination light from the epi-illumination light source.

12. The multiphoton-excitation laser scanning microscope according to claim 1, wherein the collector lens is a liquid-immersion lens with oil filling a gap between the specimen and the collector lens.

13. The multiphoton-excitation laser scanning microscope according to claim 1, wherein the light detector is disposed on an extension of the optical axis of the collector lens.

14. The multiphoton-excitation laser scanning microscope according to claim 13, wherein the light detector includes a plurality of light detector elements arranged in a two-dimensional array.

* * * * *